(12) United States Patent
Niedermeier et al.

(10) Patent No.: US 8,581,977 B2
(45) Date of Patent: Nov. 12, 2013

(54) APPARATUS AND METHOD FOR INSPECTING LABELED CONTAINERS

(75) Inventors: Anton Niedermeier, Offenstetten (DE); Rainer Kwirandt, Barbing (DE)

(73) Assignee: Krones AG, Neutraubling (DE)

( * ) Notice: Subject to any disclaimer, the term of this patent is extended or adjusted under 35 U.S.C. 154(b) by 329 days.

(21) Appl. No.: 12/868,805

(22) Filed: Aug. 26, 2010

(65) Prior Publication Data

US 2011/0050884 A1    Mar. 3, 2011

(30) Foreign Application Priority Data

Aug. 28, 2009   (DE) .................... 10 2009 039 254

(51) Int. Cl.
*H04N 7/18* (2006.01)
(52) U.S. Cl.
USPC ........................................ 348/127; 356/237.1
(58) Field of Classification Search
None
See application file for complete search history.

(56) References Cited

U.S. PATENT DOCUMENTS

| | | | | |
|---|---|---|---|---|
| 2,783,389 | A * | 2/1957 | Cummings et al. | 250/214 R |
| 3,133,638 | A * | 5/1964 | Calhoun | 209/524 |
| 3,932,042 | A * | 1/1976 | Faani et al. | 356/239.4 |
| 4,376,951 | A * | 3/1983 | Miyazawa | 348/127 |
| 4,902,137 | A * | 2/1990 | Krieg et al. | 356/427 |
| 5,794,788 | A * | 8/1998 | Massen | 209/524 |
| 6,452,156 | B2 | 9/2002 | Lindner | |
| 6,452,670 | B1 * | 9/2002 | Bour et al. | 356/237.1 |
| 7,057,718 | B2 | 6/2006 | Kwirandt | |
| 2005/0002020 | A1 * | 1/2005 | Inoue et al. | 356/237.1 |
| 2005/0139792 | A1 * | 6/2005 | Rivera et al. | 250/559.45 |
| 2006/0000968 | A1 * | 1/2006 | Katayama et al. | 250/223 B |
| 2006/0049369 | A1 * | 3/2006 | Meinhart et al. | 250/573 |
| 2006/0095778 | A1 * | 5/2006 | He et al. | 713/180 |
| 2008/0030719 | A1 | 2/2008 | Inoue et al. | |

FOREIGN PATENT DOCUMENTS

| | | |
|---|---|---|
| DE | 9311405 U1 | 9/1994 |
| DE | 29502708 U1 | 4/1996 |
| DE | 10027226 C1 | 10/2001 |
| DE | 102005023534 A1 | 11/2006 |
| DE | 102005050902 A1 | 5/2007 |
| DE | 20122829 U1 | 4/2008 |
| EP | 1143237 A1 | 10/2001 |
| EP | 1724569 A2 | 11/2006 |
| EP | 1724569 A2 * | 11/2006 |
| WO | WO-03/016886 A1 | 2/2003 |
| WO | WO/03/104780 * | 12/2003 |
| WO | WO-03/104780 A1 | 12/2003 |
| WO | WO-03104780 A1 | 12/2003 |

OTHER PUBLICATIONS

Chinese Search Report for 201010269020.0 mailed Feb. 28, 2012.
Machine translation of Kamakura, WO/2003/104780, Dec. 2003.
German Search Report for Appl. No. 10 2009 039254.8, dated Apr. 8, 2013.
Chinese Office Action for Application No. 2010102690200, dated May 29, 2013.

* cited by examiner

*Primary Examiner* — Sath V Perungavoor
*Assistant Examiner* — Dakshesh Parikh
(74) *Attorney, Agent, or Firm* — Marshall, Gerstein & Borun LLP

(57) ABSTRACT

An apparatus and a method for inspecting labeled containers, allowing a detection of holes in the label, with a high hit rate, even in cases where the color of the label is similar to that of the filled product, wherein the label is irradiated with visible light and invisible light and/or is imaged in incident light and transmitted light.

15 Claims, 3 Drawing Sheets

APPARATUS AND METHOD FOR INSPECTING LABELED CONTAINERS

CROSS-REFERENCE TO RELATED APPLICATION

The present application claims the benefit of priority of German Application No. 102009039254.8, filed Aug. 28, 2009. The entire text of the priority application is incorporated herein by reference in its entirety.

FIELD OF THE DISCLOSURE

The disclosure relates to an apparatus for inspecting labeled containers according to the preambles of claims 1 and 4 as well as to a method for inspecting labeled containers.

BACKGROUND

In order to inspect film labels shrunk on bottles or other containers, it is known e.g. from patent DE 10 2005 023 534 B4 to conduct bottles to be inspected, which are placed on a linear conveyor belt, through an inspection unit comprising two cameras and a mirror cabinet so as to image the whole circumference of the label simultaneously. The apparatus described further comprises an arena-like arrangement of lateral light screens, the illumination-side and the imaging-side beam paths having provided therein linear polarizing filters with intersecting polarizing planes so as to suppress disturbing reflections of the light screens in the recorded images.

When the film labels are inspected with respect to an existence of holes and/or fissures, the problem arises, in particular in areas of the label whose color is similar to that of the material filled in the container, that such faulty locations can only be detected with very great effort and/or cannot be detected reliably because the contrast between such locations and the surrounding label is weak.

Up to now, attempts have been made to solve this problem by comparing the acquired image data with reference pictures of the shrunk-on label. In practice, this is, however, difficult due to the fact that the position of the label on the bottle may vary, a circumstance leading, especially in the case of bottle surfaces with non-uniform curvatures, to different distortions of the label imprint. Hence, large tolerance ranges between the inspected label and the reference have to be admitted, whereby the reliability of recognition will be reduced. In addition, when the labels are changed frequently and/or in the case of changes in the imprint, many reference pictures and additional calibrations are necessary, which are cumbersome to handle.

SUMMARY OF THE DISCLOSURE

An aspect of the disclosure is achieved by means of an apparatus in which the illumination unit comprises at least two separately controllable light screens which are directed onto circumferentially substantially opposed areas of the label for selectively irradiating these areas in transmitted light and/or incident light. Especially in the case of a clear filled product, holes in the label can thus be represented as a bright image against a dark background or as a dark image against a bright background.

An advantageous embodiment additionally comprises a control unit, which is able to control the illumination unit and the camera such that imaging of the label areas takes place alternately in transmitted light and in incident light. It is thus possible to image a view of the label in two pictures which are different in contrast, so that additional image information can be used and the quality of inspection improved.

Another advantageous embodiment additionally comprises an evaluation unit, which is adapted to be used for comparing the label images recorded in transmitted light with label images recorded in incident light, and/or for setting these images off against one another. Holes and fissures can thus be shown in a representation which is particularly high in contrast.

Alternatively, the technical task is also solved by an apparatus in which the illumination unit is configured such that it is able to selectively irradiate the label with visible light and invisible light, in particular infrared light. In infrared light the contrast between a hole and the surrounding label is particularly high, since the label imprint absorbs in IR less light than the content of the bottle and appears therefore brightly in the image. It follows that the illumination can be varied, depending on the label imprint and the color of the bottle content, and this will increase the label inspection hit rate especially when the bottle content is turbid.

An advantageous embodiment additionally comprises a control unit, which is able to control the illumination unit and the camera such that the imaging of the label takes place alternately in visible light and invisible light. A view of the label can thus be imaged in two pictures which are different in contrast, so that additional image information can be used and the quality of inspection improved.

Another advantageous embodiment additionally comprises an evaluation unit, which is adapted to be used for comparing the label images recorded in visible light with label images recorded in invisible light, and/or for setting these images off against one another. Holes and fissures can thus be shown in a representation which is particularly high in contrast.

The camera is preferably arranged such that it is pointed at the label at an angle of at least 75° relative to the vertical axis of the container, and the illumination unit is configured such that it is capable of illuminating the label at an angle, which does not exceed 60°, relative to the vertical axis of the container obliquely from above and/or from below. Reflections on the bottle surface and/or on the label can thus be reduced independently of the spectral region used.

According to a preferred embodiment, the apparatus further comprises at least one illumination-side polarizing filter, which linearly polarizes light in a first direction, and at least one imaging-side linear polarizing filter having a second polarizing direction which is oriented substantially orthogonal to the first direction. Reflections on the bottle surface and/or on the label can thus be suppressed in a particularly effective manner, especially in the visible spectral region.

The camera has preferably a double exposure function which allows buffering of a first camera image so that a second camera image can be recorded before the first camera image has been fully read. It is thus possible to record two images of the label in rapid succession with an only small lateral offset in the camera image.

The technical task is additionally solved with a method comprising the following steps: a) illuminating a first circumferential subarea of a label attached, in particular by shrinking on, to a container to be inspected, and imaging a second circumferential subarea of the thus illuminated label in transmitted light in at least one camera image; and b) illuminating the second circumferential subarea of the label and imaging said second circumferential subarea in incident light in at least one camera image. Especially in the case of a clear filled product, holes in the label can thus be represented as a bright image against a dark background or as a dark image against a bright background.

According to a preferred embodiment, the label is illuminated with infrared light in steps a) and b). The holes can thus be better delimited, since most of the colors of the film labels are IR transmitting. This has the effect that less disturbing structures will be visible on the label as well as in the holes.

Alternatively, the technical task is also solved by a method comprising the following steps: a) illuminating with visible light a label attached, in particular by shrinking on, to a container to be inspected, and imaging the thus illuminated label in at least one camera image; and b) illuminating the label with invisible light, in particular infrared light, and imaging the thus illuminated label in at least one camera image. When the bottle content is turbid, the contrast between a hole and the surrounding label will, in particular in IR, increase, since the label imprint will absorb in IR less light than the bottle content and therefore appear brightly in the image. Due to the different illuminations, image data sets with differently high contrasts between the bottle content and the label can be acquired, and this will increase the hit rate of label inspection.

According to a preferred embodiment, the method additionally comprises the following steps: c) comparing and/or processing the camera images so as to detect holes and/or fissures in the label. By directly comparing respective corresponding images, defects in the label can be represented such that they are particularly high in contrast and can therefore be identified more easily.

Preferably, a mask for delimiting the holes and/or fissures is produced in step c) from the camera image recorded in step b). It is thus possible to limit a detailed examination and/or analysis of data to equivocal areas and to utilize computing capacity in a more effective manner.

According to a preferred embodiment, the camera images are recorded in steps a) and b) at time intervals of 1 ms at the most, in particular 500 µs at the most. This has the effect that, in the respective images to be compared, the label will be imaged with a largely identical perspective distortion, whereby the images can be evaluated more easily.

BRIEF DESCRIPTION OF THE DRAWINGS

A preferred embodiment of the disclosure is shown in the drawing, in which.

DETAILED DESCRIPTION OF THE PREFERRED EMBODIMENT

Figure 1:
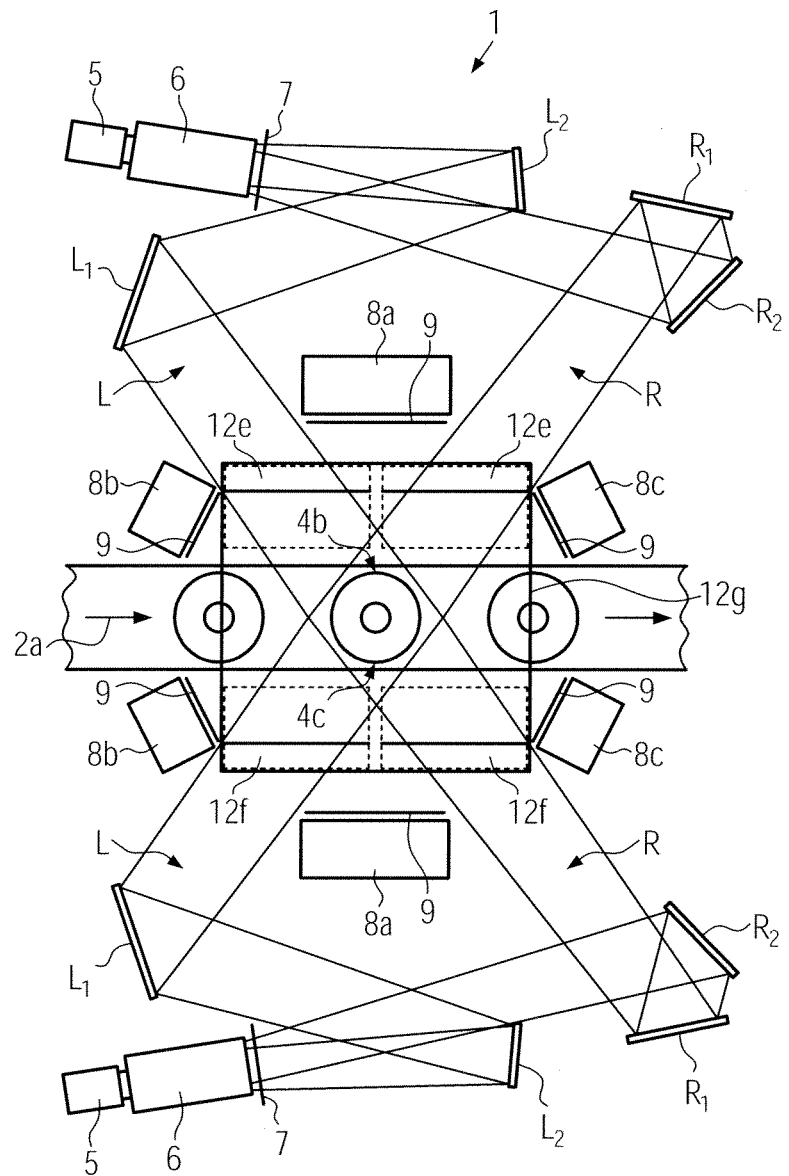
FIG. 1 shows a schematic top view of an embodiment according to the present disclosure.

The apparatus 1 comprises a straight conveyor belt 2 for continuously conveying labeled bottles 3 or other containers made of glass, plastic, or some other suitable transparent material. The respective circumferential surfaces of the bottles 3 are fully enclosed by a label 4, in particular by a shrunk-on film label, which clings closely to the outer contours of the bottle 3. The label 4 may consist of an at least partially transparent plastic film, e.g. of PE or PP, provided with a product and/or bottle-dependent imprint.

On either side of the conveyor belt 2, two cameras 5 with lenses 6 and imaging-side linear polarizing filters 7 are arranged one on top of the other and substantially axially symmetric with the conveyor belt 2, the cameras 5 being directed onto mirrors L2 and R2. The essentially vertically arranged mirror L2 forms together with a further essentially vertically arranged mirror L1 a left imaging-side beam path L, whereas the correspondingly arranged mirrors R1 and R2 form a right imaging-side beam path R. The beam paths L and R, which are oriented transversely to the conveyor belt 2, intersect with their optical axes approximately centrally above the conveyor belt 2 at a common angle of e.g. 74° and define in the area of intersection an inspection zone in which the circumferential surface of a bottle 3 to be inspected is imaged from two circumferentially displaced directions onto the respective camera 5 associated therewith. In order to obtain images of identical size, the lengths of the beam paths L and R are identical from the cameras 5, i.e. the lenses 6 up to the point of intersection of the optical axes of the two beam paths L, R. The height positions of the cameras 5 are chosen such that the respective camera is pointed, substantially centrally and approximately horizontally, at the bottle 3 and the label 4 to be inspected, in particular such that the vertical observation angle □ between the central beam LM, RM of the beam paths L, R and the main axis 3a of the container 3 amounts to at least 75°.

Figure 2:
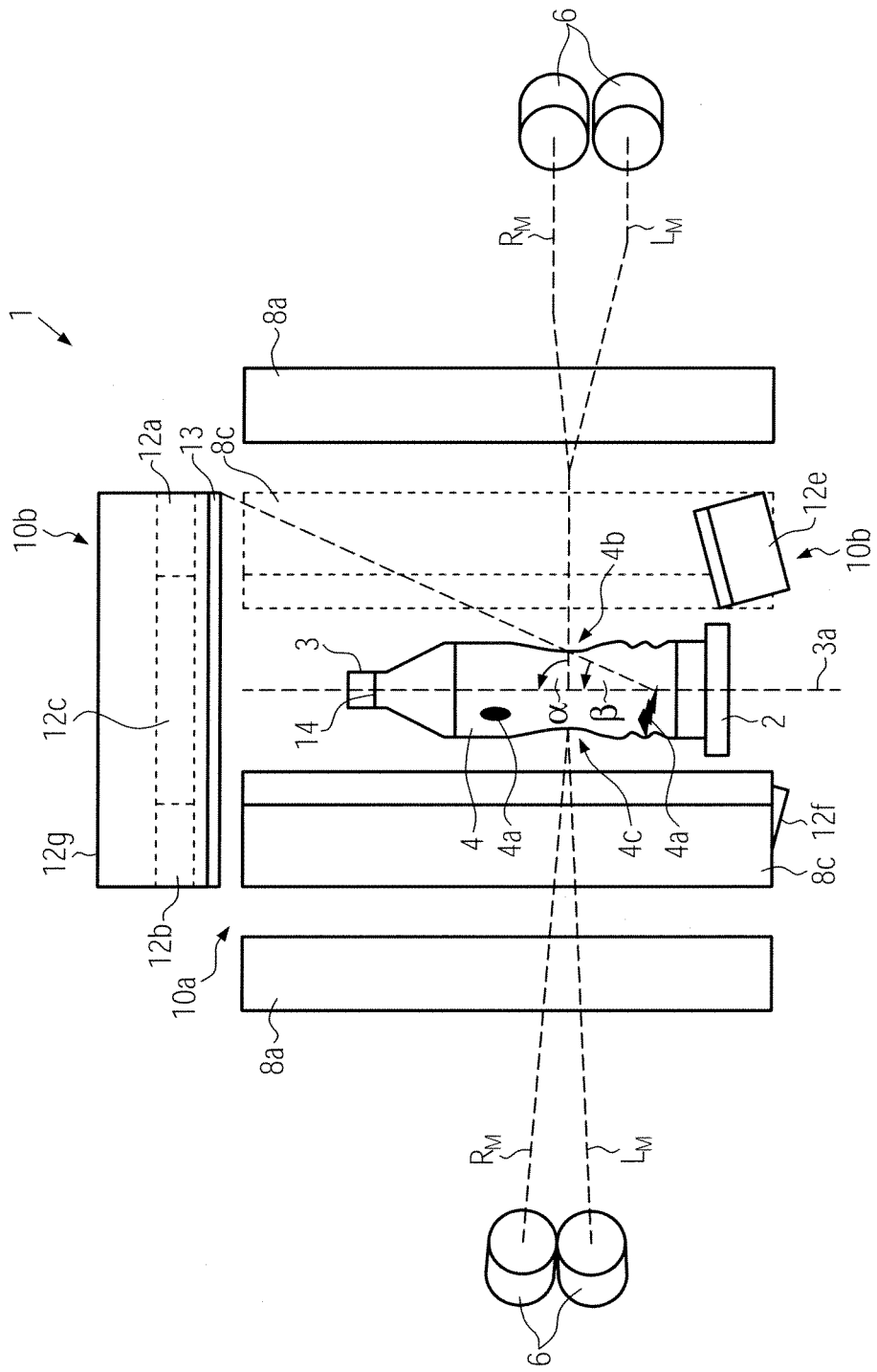
FIG. 2 shows a schematic front view of the arrangement according to FIG. 1.

As can be seen from FIG. 2, the cameras 5 are arranged one on top of the other in pairs, and the beam paths L, R can be oriented vertically, e.g. by tilting the cameras 5 and/or the mirrors L1, L2 and R1, R2. These variants are indicated in FIG. 2 on different sides of the inspection apparatus 1, the mirrors L1, L2, R1, R2 as well as polarizing filters 7 being here not shown for the sake of clarity of the representation. The cameras 5 may, however, also be arranged side by side in pairs.

Due to the fact that the cameras 5, the lenses 6 with the polarizing filters 7 and the mirrors L1, L2, R1, R2 are arranged axially symmetric with the conveyor belt 2, the whole circumference of the bottle 3 is imaged in four overlapping camera images. The number of cameras 5 and of bottle images or camera images may, however, also deviate from this.

A light screen 8a, whose main direction of emission is oriented substantially orthogonally to the conveying direction 2a of the conveyor belt 2 and the main axis 3a of the bottle 3, is provided between the two beam paths L and R. The beam paths L and the conveyor belt 2 as well as the beam paths R and the conveyor belt 2 have provided between them a respective light screen 8b and 8c. The main direction of emission of the respective light screens 8b and 8c encloses an acute angle with the conveying direction of the conveyor belt 2, the light screen 8b illuminating the bottle 3 to be inspected substantially from the back and the light screen 8c from the front. The light exit surface of the light screen 8a is preferably twice as large as that of the light screens 8b and 8c and illuminates the bottle 3 from the side transversely to the conveying direction 2a. The light screens 8a, 8b, 8c emit light in the visible spectral region (VIS) and are arranged on either side of the conveyor belt 2 around the inspection zone in a substantially semicircular mode of arrangement; their light exit surfaces extend substantially parallel to the main axis 3a of the bottle 3.

A linear polarizing filter 9 is provided in front of each of the light screens 8a, 8b and 8c, the polarizing directions of said linear polarizing filters being oriented substantially orthogonally to the main axis 3a of the bottle 3. The imaging-side polarizing filters 7 in front of the camera lenses 6 are oriented such that their polarizing direction is substantially orthogonal to the polarizing direction of the illumination-side polarizing filters 9, i.e. the polarizing planes, which cooperate in pairs, are arranged in an intersecting mode of arrangement.

Due to the intersecting arrangement of the polarizing planes of the linear polarizing filters 7 and 9, the imaging of light components of the light screens 8a, 8b, 8c reflected by the label 4 as well as direct light irradiation from the respective light screens located in opposed relationship with a camera 5 and its beam paths are suppressed. Hence, only the light components of the light screens 8a, 8b, 8c which are diffusely reflected by the label 4 will arrive at the cameras 5.

The arena-like arrangement of the light screens 8a, 8b, 8c with the polarizing filters 9 around the inspection zone defines a first light screen group 10a of an illumination unit 10 used for illuminating the whole circumference of the label 4 in a reflection-reducing mode.

For illuminating the label 4 with light in the infrared spectral region (IR) obliquely from above and obliquely from below, a second light screen group 10b of the illumination unit 10 is additionally provided, said second group 10b comprising upper light screens 12a to 12d and lower light screens 12e, 12f. The upper light screens 12a to 12d are arranged above the inspection zone and the bottle 3 to be inspected, and preferably annularly around said bottle 3, in a common housing 12g, the lateral light screens 12a and 12b being adapted to be controlled individually and separately from the front and rear light screens 12c, 12d. The lower light screens 12e, 12f extend on either side of the conveyor belt 2 along the latter and are separately controllable as well. The light screens 12a-12f preferably emit radiation in the near-infrared region, a region in which the cameras 5 have a sufficiently high sensitivity, in particular in a spectral region of 850-950 nm. A possibly lower camera sensitivity in the infrared region may e.g. be compensated for by a higher operating current, which can be used especially in the case of ID light emitting diodes, and by the absence of attenuating polarizing filters in the beam paths of the second light screen group 10b.

Figure 3:
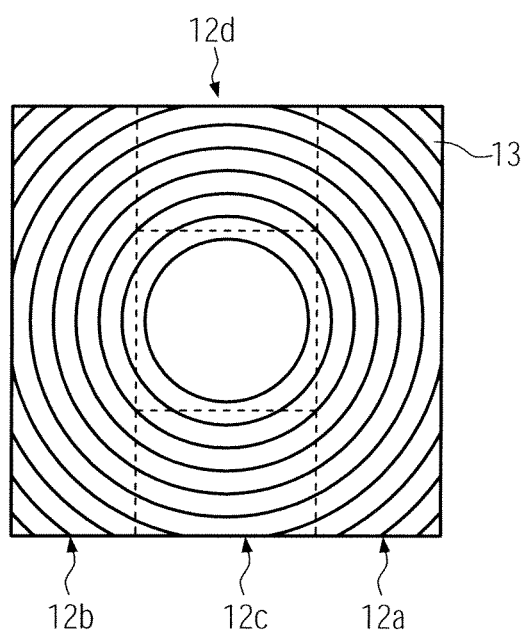
FIG. 3 shows a schematic view of a light screen with a Fresnel lens from below.

The second light screen group 10b additionally comprises Fresnel lenses 13 which concentrate the divergent light emitted by the light screens 12a-12f and deflect it obliquely downwards or upwards in the direction of the label 4. A Fresnel lens 13 can cover the light exit surfaces of a plurality of light screens 12a-12d, as indicated in FIG. 3. It is, however, also possible to provide separate lens segments. Preferably, an amount of at least 90% of the light emitted by the light screens 12a-12f impinges on the label 4 obliquely from above or below at an angle β having a maximum value of 75°, in particular not more than 60°, relative to the bottle main axis 3a, so as to largely prevent specular light reflexes from arriving at the imaging-side beam paths R, L and from being recorded by the cameras 5. The second light screen group 10b is oriented such that at least the light reflected specularly on label areas extending parallel to the bottle main axis 3a is not recoded by the cameras 5. This can be accomplished by the Fresnel lenses 13 in combination with substantially orthogonally oriented light screens, as indicated in FIG. 2 for the upper light screens 12a-12d, and/or by tilting the light screens, as indicated in FIG. 2 for the lower light screens 12e, 12f.

The focusing or concentrating effect of the Fresnel lenses 13 counteracts the beam divergence of the light screens 12a-12f and reduces in the area of the label 4 the decrease in the illumination intensity as the illumination distance from the individual light screens 12a-12f increases. This leads to a uniform illumination of the label 4.

The second light screen group 10b is suitable for illuminating the whole circumference of the label 4, viz. when all the light screens 12a-12f or at least the light screens 12a, 12b, 12e and 12f are in operation simultaneously, as well as for selectively illuminating one half of the label 4, viz. when the respective light screens 12a and 12e or 12b and 12f arranged on one side of the conveyor belt 2 are operated in common. The light falling in at an oblique angle from above and from below prevents a formation of shades on horizontally extending surface structures, such as recessed grips, ribs and beads.

The light screens 8a-8c and 12a-12f comprise preferably light emitting diode panels for the visible and infrared spectral regions; in the visible region, variously colored light emitting diodes, having e.g. the colors red, green and blue, can be combined. The illumination unit 10 may, however, be defined at least partially by a combination of VIS light emitting diodes and IR light emitting diodes in at least one common light screen 8a-8c, 12a-12f. It is imaginable to integrate separately controllable IR light emitting diodes in at least one of the light screens 8a-8c as well as to integrate separately controllable VIS light emitting diodes in at least one of the light screens 12a-12f. In addition, other pulsed light sources may be used as well. Likewise, it is possible not to provide the central light screens 12c, 12d or to screen off a central area between the lateral light screens 12a, 12b.

The polarizing filters 7 are, as such, light transmissive in the VIS as well as in the IR used, i.e. they are suitable for use with both light screen groups 10a, 10b. Furthermore, also the illumination-side polarizing filters 9 may be configured for both groups 10a, 10b with respect to their own transmission behavior as well as with respect to the light attenuation in the case of intersecting polarizing planes, in particular when VIS and IR light emitting diodes are combined in the light screens 8a-8c.

In areas in which the label is printed on with a color similar to the color of the filled product 14, IR illumination will normally allow a representation of holes and/or fissures 4a in the label 4 which is richer in contrast than a representation obtained by VIS illumination, since printing dyes will normally absorb infrared light to a much lesser extent than the filled product 14, which may e.g. be a fruit juice. In the IR exposed camera image, the label 4 will then appear brighter than the product 14 shining through a hole 4a in the label 4. This effect is additionally supported by the circumstance that printing inks are normally printed on a white label film in a semitransparent manner, said white label film absorbing hardly any infrared light, but scattering diffusely to a high extent into the imaging beam paths L, R towards the cameras 5.

For selectively controlling the illumination unit 10, in particular the light screen groups 10a, 10b and/or the light screens 12a and 12e or 12b and 12f defining groups on a respective half side, in the pulsed mode of operation and for triggering the cameras 5, a control unit 15 (not shown) is provided, and for reading image data sets from the cameras 5 and evaluating the associated camera images, an evaluation unit 16 (not shown) is provided, by means of which image data sets can be represented, compared, processed and set off against one another, e.g. by subtraction or division. However, the functions of the control unit 15 and of the evaluation unit 16 may also be combined in one unit or distributed over an arbitrary number of units.

The cameras 5 are e.g. configured as CCD cameras with a surface array and they are sensitive in the VIS as well as in the IR region, in particular in a spectral region of 380-1000 nm. The cameras 5 normally have a double exposure function, which allows two separately evaluable camera images to be recorded in rapid succession, especially within a period of 1 ms. In so doing, the data set of the second camera image can be generated before the data set of the first camera image has been read completely from the camera 5. The double exposure function thus allows buffering of image data in the camera so as to obtain two pictures of the label 4 with the least possible lateral offset of the bottle 3 moving through the image area. The reading of the image data, which takes a comparatively long time, can then be executed before the next bottle 3 arrives at the inspection zone. Alternatively, it is, however, also possible to provide additional cameras 5 for recording a plurality of camera images at short intervals or a the same time.

It follows that, making use of the embodiment described, two panorama images of the whole circumference of the label 4 can be recorded in rapid succession by suitable triggering of the illumination unit 10, each of said panorama images being based on four overlapping individual images.

Adjustment possibilities for optimizing the inclination and the angle of rotation of the light screens and polarizing filters, respectively, are generally known and therefore not described in detail. For further optimization, non-labeled areas of the bottle can be screened off.

The combination of the light screen groups 10a and 10b offers the advantage that low-reflection illumination beam paths for different spectral regions can be formed independently from one another and at a reasonable price, in particular in comparison with combined beam paths with broadband VIS/IR polarizing filters.

The embodiment offers maximum flexibility through selective irradiation in different spectral regions and/or of subareas 4b, 4c of the label 4. Depending on the requirements to be satisfied, one of the light screen groups 10a, 10b may, however, suffice. Likewise, it may suffice to image the label 4 only with illumination in different spectral regions in incident light or with half-side illumination in one spectral region, in particular in IR. As will be described herein below, a change of spectral regions offers advantages especially when the products 14 in question are turbid, whereas half-side illumination and imaging in transmitted light and/or incident light can advantageously be used in particular for clear products 14.

By varying the illumination control and by evaluating the images in a suitable manner, the inspection apparatus 1 according to the present disclosure can be used e.g. for the modes of operation described in the following:

Especially when the filled product is turbid, a panorama image of the circumference of each of the bottles 3 to be inspected is preferably recorded with infrared and with visible illumination in incident light in the most rapid possible succession. To this end, the bottles 3 are conveyed continuously, one after the other and at a suitable distance from one another, on the conveyor belt 2 into the inspection zone, where they are inspected. As soon as the respective bottle 3 arrives at a specific inspection position in the imaging area of the camera 5, the illumination unit 10 is first triggered by the control unit 15 such that it will emit a VIS flash, in the present example with the light screens 8a-8c, and that a first panorama image of the label 4 will be recorded by the cameras 5. The image data generated are buffered in the cameras 5, in particular in the surface arrays thereof, so that a second image can be recorded in rapid succession with the same camera 5, already before the image data have fully been read.

With a temporal offset of not more than 1 ms, preferably not more than 500 μs, from the moment at which the VIS flash was triggered, the illumination unit 10 is triggered such that it will emit an IR flash, in the present example with the light screens 12a-12f. During the IR flash, the cameras 5 record a second panorama image of the label 4, the spatial offset of the bottle 3 in the camera image between the first image in the visible spectral region and the second image in the infrared region being minimized by the double exposure of the cameras 5 and the resultant short period between the moments of triggering. The images may also be recorded in reverse sequence.

The image data of the VIS and of the IR image are read from the cameras 5 and processed in the evaluation unit 16. Reading of the respective first camera image can already be started while the second camera image is still being recorded. The camera images can be compared in the evaluation unit 16, the imprint areas of the label 4, which appear with differently high contrasts in the IR and VIS images, increasing the probability that a hole 4a or a fissure in the label can be detected, in particular in areas where the label imprint has a color similar to that of the product 14.

It is also possible to filter the IR and VIS images and/or to set them off against one another, e.g. by means of subtraction or division. Another possibility of image processing and defect recognition is to form a mask on the basis of an image, e.g. an IR image, for delimiting potential defect zones in the label 4, and to subsequently examine these potential defect zones in detail on the basis of the second image or on the basis of a combination of IR and VIS images.

An alternative method can be used advantageously in particular for clear products 14, said method comprising the step of recording, in the most rapid possible succession and with half-side, in particular infrared illumination, a panorama image of the circumference of each of the bottles 3 to be inspected. The course of action corresponds generally to that described hereinbefore. However, at the first triggering time only light screens on one side of the conveyor belt 2 are triggered, e.g. the screens 12a and 2e, or, depending on the equipment of the light screens with various VIS/IR/UV light emitting diodes, alternatively the screens 8a, 8b and 8c on the respective side of the conveyor belt 2, whereby the circumferential label area 4b is recorded in incident light and the area 4c is recorded in transmitted light. At the second triggering time, only the corresponding light screens on the other side are triggered, in present example the screens 12b and 12f, whereby the circumferential label area 4c is recorded in incident light and the area 4b is recorded in transmitted light.

By means of this illumination, the areas 4b, 4c of the label 4, which are arranged in a substantially opposed relationship with one another in the circumferential direction, and therefore also possibly existing holes 4a are imaged in the panorama image by the cameras 5 alternately in transmitted light and incident light, respectively. Two triggering times will here suffice for imaging the whole circumference of the label 4 in transmitted light as well as in incident light.

Especially when the product in question is a clear product 14, this has the effect that the holes 4a appear bright in the transmitted light, since, depending on the imprint, the illumination of the opposite side will partially penetrate the label 4, and the thus illuminated back of the label 4 will be visible through the holes 4a. On the other hand, the holes 4a will appear in incident light darker than the label 4, since backscattering in the clear product 14 is low and since the opposite side of the label 4 will not be illuminated. Depending on the diameter of the bottle 3 and the turbidity of the product 14, this effect will, in a weaker form, also occur in the case of turbid products 14.

When corresponding transmitted light and incident light images are filtered and/or combined in image processing, the holes 4a and/or fissures can be represented with a particularly high contrast. As has been described hereinbefore, the transmitted light and incident light images may be used for producing a mask so as to delimit potential defect zones in the label 4. Other possibilities of image processing are the generation of pseudocolors from shades of gray for a more effective visualization of holes and fissures 4a.

Depending on the label imprint, it may, however, also suffice to evaluate only the transmitted light images or only the incident light images.

The half-side illumination could, in principle, also be executed with visible light. The IR illumination is, however, advantageous insofar as the imprint will interfere to a lesser extent with image evaluation or defect detection, since most of the printing dyes do not absorb much light in IR. It follows that the contour and/or the area of a hole 4a can in IR be delimited more easily with respect to the label imprint; this applies to incident light as well as transmitted light applications.

Depending on the number of cameras 5 and on the possibility of multiple exposure, VIS and IR illumination over the whole circumference and half-side illumination can be combined in an arbitrary manner.

It is also possible to use UV light instead of IR light. In this respect, it is of decisive importance that the absorption characteristics of the label imprint and of the product 14 differ from one another in invisible light, although the coloring in visible light is similar.

The invention claimed is:

1. An apparatus for inspecting labeled containers, comprising:
    an illumination unit for illuminating a label attached to a container to be inspected;
    at least two cameras for imaging the illuminated label in four overlapping images constituting a panorama image of the circumference of the container;
    the illumination unit being configured such that it is able to selectively irradiate the circumference of the container with visible light and invisible light, respectively; and
    an evaluation unit which is adapted to be used for comparing a first panorama image containing the label and recorded in visible light with a second panorama image containing the label and recorded in invisible light, and/or for setting these panorama images off against one another.

2. An apparatus according to claim 1, and a control unit which is able to control the illumination unit and the camera such that the imaging of the label takes place alternately in visible light and invisible light.

3. An apparatus according to claim 1, wherein the camera is arranged such that it is pointed at the label at an angle ($\alpha$) of at least 75° relative to the vertical axis of the container, and that the illumination unit is configured such that it is capable of illuminating the label at an angle ($\beta$), which does not exceed 60°, relative to the vertical axis of the container obliquely from above and/or from below.

4. An apparatus according to claim 1, and at least one illumination-side polarizing filter which linearly polarizes light in a first direction, and at least one imaging-side linear polarizing filter having a second polarizing direction which is oriented substantially orthogonal to the first direction.

5. An apparatus according to claim 1, wherein the camera has a double exposure function which allows buffering of a first camera image so that a second camera image can be recorded before the first camera image has been fully read.

6. A method of inspecting labeled containers, comprising:
    a) illuminating with visible light the circumference of a container to be inspected, and imaging a thus illuminated label in four overlapping images constituting a first panorama image of the circumference of the container;
    b) illuminating with invisible light the circumference of the container and imaging the thus illuminated label in four overlapping images constituting a second panorama image of the circumference of the container; and
    c) comparing the first panorama image with the second panorama image, and/or setting these images off against one another.

7. A method according to claim 6, and:
    in this step c) comparing and/or processing the panorama images so as to detect holes and/or fissures in the label.

8. A method according to claim 7, and in step c), using the panorama image recorded in step b) for producing therefrom a mask for delimiting the holes and/or fissures.

9. A method according to claim 6, wherein the camera images are recorded in steps a) and b) at time intervals of 1 ms at the most.

10. An apparatus according to claim 1, wherein the label is attached to the container by shrinking on.

11. An apparatus according to claim 1, wherein the label is attached to the container by shrinking on.

12. An apparatus according to claim 1, wherein the invisible light is infrared light.

13. A method according to claim 6, wherein the label is attached to the container by shrinking on.

14. A method according to claim 6, wherein the invisible light is infrared light.

15. A method according to claim 9, wherein the time intervals is 500 µs at the most.

* * * * *